US012765837B2

(12) United States Patent
Dwarika

(10) Patent No.: US 12,765,837 B2
(45) Date of Patent: *Oct. 20, 2026

(54) RESPIRATORY DISEASE MONITORING WEARABLE APPARATUS

(71) Applicant: HEALTH CARE ORIGINALS, INC., Rochester, NY (US)

(72) Inventor: Jared Dwarika, Rochester, NY (US)

(73) Assignee: HEALTH CARE ORIGINALS, INC., Rochester, NY (US)

( * ) Notice: Subject to any disclaimer, the term of this patent is extended or adjusted under 35 U.S.C. 154(b) by 761 days.

This patent is subject to a terminal disclaimer.

(21) Appl. No.: 17/650,958

(22) Filed: Feb. 14, 2022

(65) Prior Publication Data

US 2022/0167917 A1 Jun. 2, 2022

Related U.S. Application Data

(63) Continuation-in-part of application No. 15/147,293, filed on May 5, 2016, now Pat. No. 11,272,864.
(Continued)

(51) Int. Cl.
*A61B 5/00* (2006.01)
*A61B 5/08* (2006.01)
(Continued)

(52) U.S. Cl.
CPC .......... *A61B 5/6823* (2013.01); *A61B 5/0002* (2013.01); *A61B 5/0823* (2013.01);
(Continued)

(58) Field of Classification Search
None
See application file for complete search history.

(56) References Cited

U.S. PATENT DOCUMENTS 5,226,424 A * 7/1993 Bible .................... A61B 5/335 600/508
6,168,568 B1 1/2001 Gavriely
(Continued)

FOREIGN PATENT DOCUMENTS

CN 102015037 A 4/2011
CN 102293992 A 12/2011
(Continued)

OTHER PUBLICATIONS

International Preliminary Report on Patentability (Chapter II) dated May 17, 2024 from PCT Application No. PCT/2023/061700 (24 pages).

(Continued)

*Primary Examiner* — Meredith Weare
(74) *Attorney, Agent, or Firm* — INNOVATION CAPITAL LAW GROUP, LLP; Vic Lin

(57) ABSTRACT

A monitoring and alerting system can be used in any condition with a respiration component. Respiratory symptoms as well as supporting physiological functions are tracked against the user's baseline and alerts the user when there is a worsening trend. The system is self-contained in a wearable that detects and logs the signals, analyzes them and generates alerts. The wearable is untethered during use and may be attached to the body in various manners, such as with adhesives, clothing, clips, belts, chains, necklaces, ear pieces, clothing circuits or the like. Information can further be transmitted both wirelessly and via wire to devices, cloud storage, or the like.

10 Claims, 5 Drawing Sheets

Related U.S. Application Data

(60) Provisional application No. 62/218,109, filed on Sep. 14, 2015.

(51) Int. Cl.
*A61B 5/113* (2006.01)
*A61B 7/00* (2006.01)

(52) U.S. Cl.
CPC ............ *A61B 5/113* (2013.01); *A61B 5/7221* (2013.01); *A61B 5/7282* (2013.01); *A61B 5/746* (2013.01); *A61B 7/003* (2013.01); *A61B 2562/0204* (2013.01); *A61B 2562/06* (2013.01); *A61B 2562/164* (2013.01)

(56) References Cited

U.S. PATENT DOCUMENTS

| | | | | |
|---|---|---|---|---|
| 11,272,864 | B2 * | 3/2022 | Dwarika | A61B 5/6823 |
| 2004/0186390 | A1 | 9/2004 | Ross et al. | |
| 2007/0100213 | A1 | 5/2007 | Dossas et al. | |
| 2008/0288026 | A1 | 11/2008 | Cross et al. | |
| 2009/0076405 | A1 * | 3/2009 | Amurthur | A61B 5/4818 600/529 |
| 2009/0216127 | A1 * | 8/2009 | Gavriely | A61B 5/0823 600/453 |
| 2010/0037489 | A1 | 2/2010 | Berner, Jr. et al. | |
| 2010/0228113 | A1 | 9/2010 | Solosko et al. | |
| 2011/0035158 | A1 | 2/2011 | Banos et al. | |
| 2011/0125044 | A1 * | 5/2011 | Rhee | A61B 7/003 600/534 |
| 2011/0144470 | A1 | 6/2011 | Mazar et al. | |
| 2013/0172691 | A1 | 7/2013 | Tran | |
| 2013/0173461 | A1 | 7/2013 | Levy | |
| 2013/0237863 | A1 | 9/2013 | Song et al. | |
| 2014/0221855 | A1 | 8/2014 | McCaffrey | |
| 2015/0088007 | A1 * | 3/2015 | Bardy | G16Z 99/00 600/483 |
| 2015/0126848 | A1 * | 5/2015 | Baker | A61B 5/14552 600/391 |
| 2015/0257654 | A1 * | 9/2015 | Bennett-Guerrero | A61B 5/0002 600/595 |
| 2015/0351690 | A1 | 12/2015 | Toth et al. | |
| 2016/0066837 | A1 | 3/2016 | Melo | |
| 2016/0073953 | A1 * | 3/2016 | Sazonov | A61B 5/1107 600/590 |
| 2016/0100808 | A1 | 4/2016 | Anbarani | |
| 2016/0361026 | A1 * | 12/2016 | Sarkar | A61B 5/349 |
| 2017/0071506 | A1 * | 3/2017 | Dwarika | A61B 5/08 |
| 2018/0049653 | A1 * | 2/2018 | Husheer | A61B 5/0816 |
| 2018/0325385 | A1 | 11/2018 | Deterding et al. | |
| 2019/0290150 | A1 | 9/2019 | Felix et al. | |
| 2019/0388030 | A1 | 12/2019 | Colliou et al. | |
| 2020/0188697 | A1 * | 6/2020 | Kabrams | A61B 5/4094 |
| 2021/0063434 | A1 * | 3/2021 | Laput | A61B 5/28 |
| 2021/0199477 | A1 | 7/2021 | Dwarika et al. | |
| 2024/0057963 | A1 | 2/2024 | Rimmer et al. | |
| 2024/0149052 | A1 | 5/2024 | Freeman et al. | |

FOREIGN PATENT DOCUMENTS

| | | | |
|---|---|---|---|
| CN | 202859097 | U | 4/2013 |
| CN | 205359455 | U | 7/2016 |
| CN | 106164817 | A | 11/2016 |
| WO | 2006065679 | A2 | 6/2006 |
| WO | 2008148172 | A1 | 12/2008 |
| WO | 2009096630 | A1 | 8/2009 |
| WO | 2015044851 | A2 | 4/2015 |
| WO | 2020243463 | A1 | 12/2020 |

OTHER PUBLICATIONS

International Search Report & Written Opinion dated May 26, 2023 from PCT Application No. PCT/2023/061700.

* cited by examiner

RESPIRATORY DISEASE MONITORING WEARABLE APPARATUS

CROSS-REFERENCE TO RELATED APPLICATIONS

This application is a continuation-in-part of U.S. patent application Ser. No. 15/147,293, filed May 5, 2016, the contents of which are herein incorporated by reference.

BACKGROUND OF THE INVENTION

1. Field of the Invention

One or more embodiments of the invention relates generally to monitoring and alerting systems. More particularly, the invention relates to systems and methods for monitoring and alerting a user of any condition with a respiration component.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Respiration measurements can provide insight into an individual's wellbeing. Respiration measurements can be indicative of physiological and/or mental states of an individual, as well as prognostic with regard to diagnosis of medical conditions. For example, respiration measurements can provide insight into an individual's stress levels, and can be evidential of more serious pulmonary disorders, such as disorders associated with chronic obstructive pulmonary disease (COPD) and asthma.

Asthma may be considered one of the most preventable conditions necessitating frequent use of acute care services. To prevent hospitalizations and emergency department visits, it may be important for physicians to obtain an accurate assessment of a subject's asthma symptom control. A subject's perception and caretaker's perception of asthma control of a subject may vary tremendously and frequently may not correlate with objective measures. With varying asthma phenotypes, poor asthma-control perception, and growing costs of asthma, adequate asthma-control measures are important. These control measures include methods for monitoring a user's respiration parameters to obtain an accurate assessment of the patient's symptoms.

Traditionally, however, respiration monitoring has occurred in a clinical setting, contributing to the developing of respiration monitoring devices that are non-ambulatory, lack portability, and are difficult to use. Other respiration monitoring devices are devices that are tethered to another device for full functionality.

These conventional devices include smart devices (such as smartphones) tethered to sensors with or without data-loggers where meaningful processing of the sensor data occurs on the smart device, wearables that lack the ability to detect, data-log and analyze acoustic physiological signals, wearables that have to be embodied in vests or some other system larger than the intended wearable, wearables that have wired or wireless connections to another component or device housed separately from the wearable, and wearables that attempt to detect signals that infer that the acoustic physiological signals are present.

Many of the conventional devices suffer from one or more of the following problems: bulky or heavy devices requiring equally tenuous means of securing to the body; the need for wired or wireless sensors separate from the processing and data-logging components; data needed to be processed on devices/systems detached from the sensing and/or data-logging components; heavy power consumption requiring significant amount of stored energy devices possibly working in conjunction with energy harvesting devices; the need for continuous data transfer between sensors and the processing devices; devices tend to be large due to collection of subcomponents requiring a large amount of space; devices tend to have low processing capability to compensate for size and power consumption; devices tend to have short running time due to their power hungry nature; and devices tend to require the need of other devices for complete functionality, such as additional devices to process information or transmit data over a long range.

As can be seen, there are significant pitfalls in the devices available for respiratory monitoring. This led to the evaluation of a system geared for Asthma called the Automated Device for Asthma Monitoring, where this represents the most compelling solution to date. However, this solution fails on a significant number of points raised in the above paragraphs.

In view of the foregoing, it is clear that there is a need for a device that can continuously detect, measure, record, data-log, analyze and compare with benchmarks, acoustic physiological signals, namely cardio pulmonary signals, as well as temperature and reflectance derived blood oxygen levels and capture the corresponding activity and motions in a miniature, ambulatory, autonomous, wearable device. The device should (1) provide real time monitoring of the respiratory system inclusive of acoustic physiological signals; (2) capture active data in real time; (3) have the ability to transmit meaningful data to device(s) over a broad area; (4) have a relatively small form factor; and (5) have continuous run time measured in whole days. The present invention, as described below, provides such a device which satisfies one or more of deficiencies of conventional devices.

SUMMARY OF THE INVENTION

Embodiments of the present invention provide a wearable physiological monitoring device comprising at least one sensor for measuring a physiological parameter of a user; an acoustic sensor for receiving an acoustic signal; and an integrated processor for analyzing data received from the at least one sensor and the acoustic sensor and comparing the measured physiological properties to a user's baseline.

Embodiments of the present invention further provide a wearable respiratory and physiological monitoring device comprising at least two distinct sensors for measuring physiological parameters of a user; an acoustic sensor for receiving an acoustic signal; a pre-processor for performing a first processing of a signal from the at least one sensor and the acoustic sensor; and a main processor operating periodically for analyzing data received from the at least two distinct sensors and the acoustic sensor and comparing the measured physiological properties to a user's baseline.

Embodiments of the present invention also provide a method for measuring physiological parameters of a user comprising disposing a wearable on a user; measuring at least one physiological parameter of the user with at least one sensor; measuring an acoustic signal from the user sensor with an acoustic sensor; analyzing data received from the at least one sensor and the acoustic sensor with an integrated processor; and comparing the measured physiological properties to a user's baseline.

In some embodiments, the at least one sensor includes at least two distinct sensors arranged in a sensor array.

In some embodiments, the integrated processor includes a pre-processor for performing a first processing of a signal from the at least one sensor and the acoustic sensor. A buffer/memory may be used for storing the signal after being processed by the pre-processor.

In some embodiments, the integrated processor includes a main processor, the main processor operating periodically, as defined herein. A main memory may be used for storing the signal processed by the main processor.

In some embodiments, the device can include a data communication module for sending data or an alert to an external device. The data communication module may operate periodically, as defined herein, or as required to send an alert.

The device can perform real-time, continuous monitoring measured in whole days.

Typically, the acoustic signals are detected and recorded directly from a surface of the user between a waist and a base of a neck of the user.

The sensors may be arranged in a sensor array which can include an accelerometer, a gyroscope, a microphone, a temperature sensor, a vibration sensor, an optical sensor and sensors for measuring the electrical potential of the body. Some or all sensors described above can be used according to the desired accuracy and depth of information.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

Figure 1A:
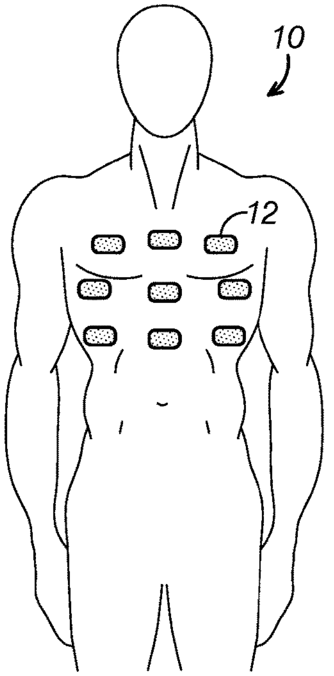
FIGS. 1A through 1C illustrate various placement options for one or more wearables on a user according to exemplary embodiments of the present invention.

Unless otherwise indicated illustrations in the figures are not necessarily drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the figures or description below.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary, a variety of optional components are described to illustrate the wide variety of possible embodiments of the present invention.

A "computer" or "computing device" may refer to one or more apparatus and/or one or more systems that are capable of accepting a structured input, processing the structured input according to prescribed rules, and producing results of the processing as output. Examples of a computer or computing device may include: a computer; a stationary and/or portable computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a client; an interactive television; a web appliance; a telecommunications device with internet access; a hybrid combination of a computer and an interactive television; a portable computer; a tablet personal computer (PC); a personal digital assistant (PDA); a portable telephone; application-specific hardware to emulate a computer and/or software, such as, for example, a digital signal processor (DSP), a field programmable gate array (FPGA), an application specific integrated circuit (ASIC), an application specific instruction-set processor (ASIP), a chip, chips, a system on a chip, or a chip set; a data acquisition device; an optical computer; a quantum computer; a biological computer; and generally, an apparatus that may accept data, process data according to one or more stored software programs, generate results, and typically include input, output, storage, arithmetic, logic, and control units.

"Software" or "application" may refer to prescribed rules to operate a computer. Examples of software or applications may include: code segments in one or more computer-readable languages; graphical and or/textual instructions; applets; pre-compiled code; interpreted code; compiled code; and computer programs.

The example embodiments described herein can be implemented in an operating environment comprising computer-executable instructions (e.g., software) installed on a computer, in hardware, or in a combination of software and hardware. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software program code for carrying out operations for aspects of the present invention can be written in any combination of one or more suitable programming languages, including an object oriented programming languages and/or conventional procedural programming languages, and/or programming languages such as, for example, Hypertext Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Wireless Markup Language (WML), Java™, Jini™, C, C++, Smalltalk, Python, Perl, UNIX Shell, Visual Basic or Visual Basic Script, Virtual Reality Markup Language (VRML), ColdFusion™ or other compilers, assemblers, interpreters or other computer languages or platforms.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). The program code may also be distributed among a plurality of computational units wherein each unit processes a portion of the total computation.

The Internet is a worldwide network of computers and computer networks arranged to allow the easy and robust exchange of information between computer users. Hundreds of millions of people around the world have access to computers connected to the Internet via Internet Service Providers (ISPs). Content providers (e.g., website owners or operators) place multimedia information (e.g., text, graphics, audio, video, animation, and other forms of data) at specific locations on the Internet referred to as webpages. Web sites comprise a collection of connected, or otherwise related, webpages. The combination of all the web sites and their corresponding webpages on the Internet is generally known as the World Wide Web (WWW) or simply the Web. Although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

It will be readily apparent that the various methods and algorithms described herein may be implemented by, e.g., appropriately programmed general purpose computers and computing devices. Typically, a processor (e.g., a microprocessor) will receive instructions from a memory or like device, and execute those instructions, thereby performing a process defined by those instructions. Further, programs that implement such methods and algorithms may be stored and transmitted using a variety of known media.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The term "computer-readable medium" as used herein refers to any medium that participates in providing data (e.g., instructions) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASHEEPROM, any other memory chip or cartridge, a carrier wave as described hereinafter, or any other medium from which a computer can read.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols, such as Bluetooth, TDMA, CDMA, 3G.

Where databases are described, it will be understood by one of ordinary skill in the art that (i) alternative database structures to those described may be readily employed, (ii) other memory structures besides databases may be readily employed. Any schematic illustrations and accompanying descriptions of any sample databases presented herein are exemplary arrangements for stored representations of information. Any number of other arrangements may be employed besides those suggested by the tables shown. Similarly, any illustrated entries of the databases represent exemplary information only; those skilled in the art will understand that the number and content of the entries can be different from those illustrated herein. Further, despite any depiction of the databases as tables, an object-based model could be used to store and manipulate the data types of the present invention and likewise, object methods or behaviors can be used to implement the processes of the present invention.

Embodiments of the present invention may include apparatuses for performing the operations disclosed herein. An apparatus may be specially constructed for the desired purposes, or it may comprise a general-purpose device selectively activated or reconfigured by a program stored in the device.

Unless specifically stated otherwise, and as may be apparent from the following description and claims, it should be appreciated that throughout the specification descriptions utilizing terms such as “processing,” “computing,” “calculating,” “determining,” or the like, refer to the action and/or processes of a computer or computing system, or similar electronic computing device, that manipulate and/or transform data represented as physical, such as electronic, quantities within the computing system’s registers and/or memories into other data similarly represented as physical quantities within the computing system’s memories, registers or other such information storage, transmission or display devices.

In a similar manner, the term “processor” may refer to any device or portion of a device that processes electronic data from registers and/or memory to transform that electronic data into other electronic data that may be stored in registers and/or memory or may be communicated to an external device so as to cause physical changes or actuation of the external device.

Broadly, embodiments of the present invention relate to a monitoring and alerting system for use in any condition, especially those with a respiration component. Respiratory symptoms as well as supporting physiological functions are tracked against the user’s baseline and alerts the user when there is a worsening trend. The system is self-contained in a wearable that detects and logs the signals, analyzes them and generates alerts. The wearable is untethered during use and may be attached to the body in various manners, such as with adhesives, clothing, clips, belts, chains, necklaces, ear pieces, clothing circuits or the like. Information can further be transmitted both wirelessly and via wire to devices, cloud storage, or the like.

Currently, there are no continuous monitoring, miniature, ambulatory, autonomous respiratory devices that detect and measure conventional symptoms similar to general office practice equipment, such as a thermometer, a stethoscope, a blood oxygen meter and a sphygmomanometer. Moreover, there is currently no continuous monitoring, miniature, ambulatory, autonomous devices that measures a user’s temperature, blood oxygen concentration, pulse and blood pressure while simultaneously recording activity information that is further analyzed to identify abnormalities. Further, there are currently no continuous monitoring, miniature, perambulatory, autonomous devices that accomplishes at least two distinct measurements and determines the user’s baseline with the intent to indicate when symptoms are worsening as compared with the self-generated baselines. The present invention provides devices, systems, and methods that provide these features that were previously lacking in the art.

Moreover, currently, there are no ambulatory devices for extended real time use that can detect and monitor an array of body signals, where acoustic signals are key, such as where acoustic signals need to be detected and recorded directly from the surface of the body (i.e., contact sensing) between the waist and the base of the neck. This is different from attempting to collect audio signals via a device or microphone loosely attached/worn to the body, or on an appendage or on the neck or as an earpiece. Also, there are no ambulatory devices where the acoustic signals are accompanied by motion of the upper torso so that this motion is also detected and matched with the audio for time correlation. The available devices on the market either measure a variety of signals except acoustic or short term acoustic only. The closest devices are point of care or bedside implemented.

Acoustic signals are key for many applications ranging from cardiology use to respiratory. To date, almost all cardiology applications are implemented as non-acoustic systems, but this now makes it possible for acoustic implementation.

These implementations are for the gathering of data over a period of time to aid in treatment and or diagnosis. The analysis is dependent on the end user processing the signals accordingly. Additionally, it is for use in a nonprofessional capacity for general wellness, the applications of which are numerous and growing each day.

The device and system of the present invention can continuously detect, measure, record, data-log, analyze and compare with benchmarks, acoustic physiological signals, namely cardio pulmonary signals, as well as temperature and reflectance derived blood oxygen levels and capture the corresponding activity and motions in a miniature, ambulatory, autonomous, wearable device. The device and system of the present invention can (1) provide real time monitoring of the respiratory system inclusive of acoustic physiological signals; (2) capture active data in real time; (3) have the ability to transmit meaningful data to device(s) over a broad area; (4) have a relatively small form factor; and (5) have continuous run time measured in whole days.

Figure 1B:
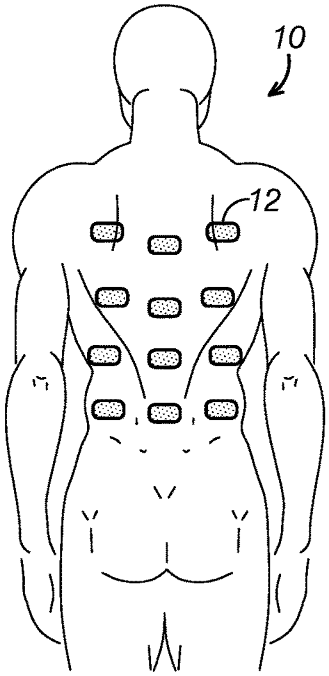
Figure 1C:
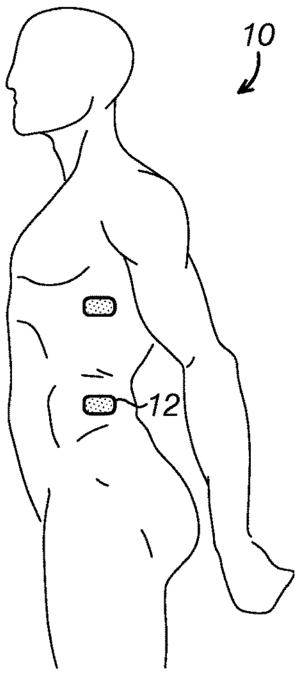

FIGS. 1A through 1C illustrate a wearable 12 attached to a user 10. Typically, a single wearable 12 can be attached and includes multiple functions, as discussed below, built therein. In some embodiments, more than one wearable 12 may be worn by the user at different locations. For example, where it is desired to detect wheezing or rales in each lung separately, two wearables 12 may be worn at each lung location. FIGS. 1A through 1C show examples of various locations where one or more of the wearables 12 may be positioned on the body of the user 10. Of course, other locations outside of those specifically shown are contemplated within the scope of the present invention.

Figure 2:
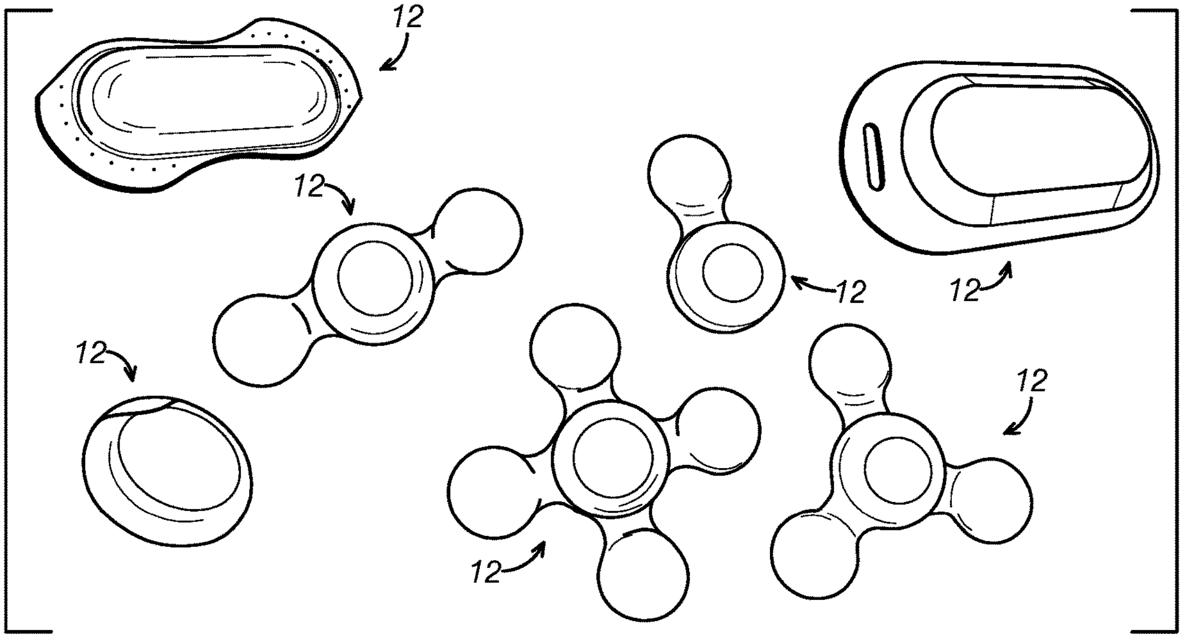
FIG. 2 illustrates various configurations for the wearables shown in FIGS. 1A through 1C.

The wearable 12 can take the form of various shapes or sizes. FIG. 2 shows examples of various shapes and sizes of the wearable 12. In some embodiments, the specific size and shape may depend on the specific application, the desired wear location, activity level of the user, or the like.

Figure 3:
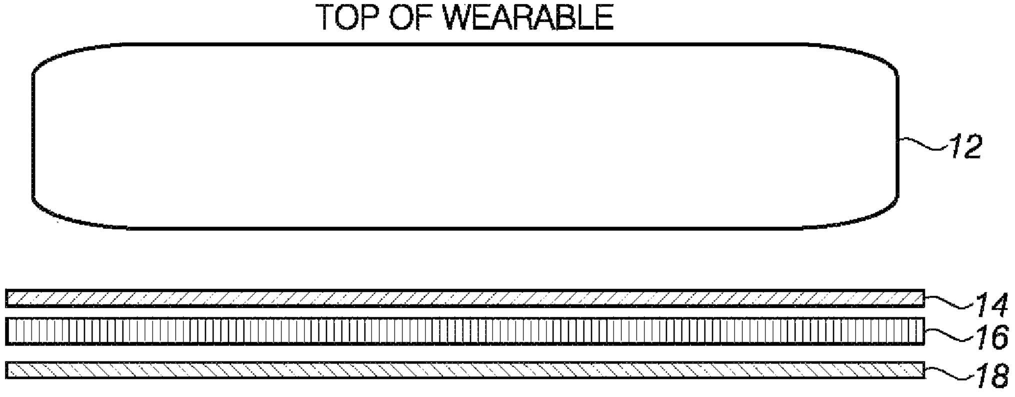
FIG. 3 illustrates a side view of a wearable according to an exemplary embodiment of the present invention.

Referring to FIG. 3, when the wearable 12 is attached to the skin surface, the wearable 12 may be attached to a mounting material 16 via an adhesive 14, for example. The mounting material 16 can then be attached to the skin of the user 10 with an adhesive 18 for bonding with the skin.

Figure 4:
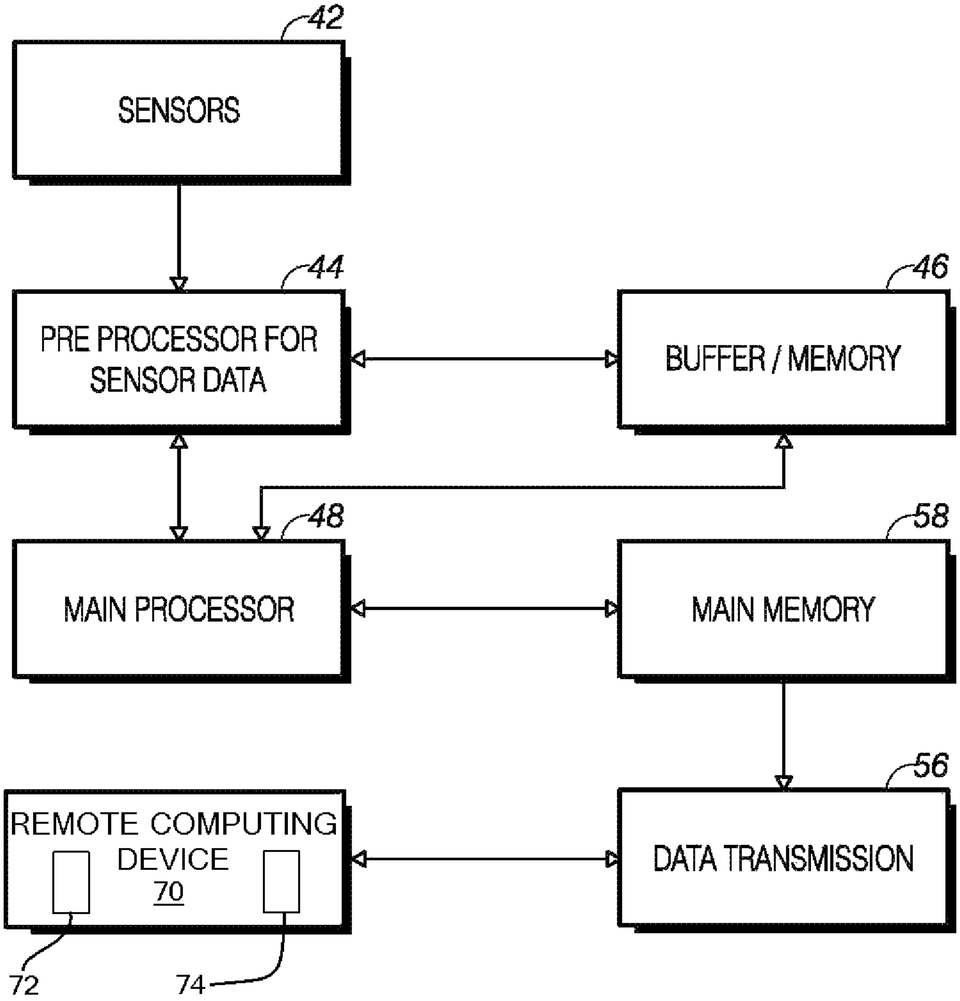
FIG. 4 illustrates exemplary processing performed within a wearable according to an exemplary embodiment of the present invention.
Figure 5:
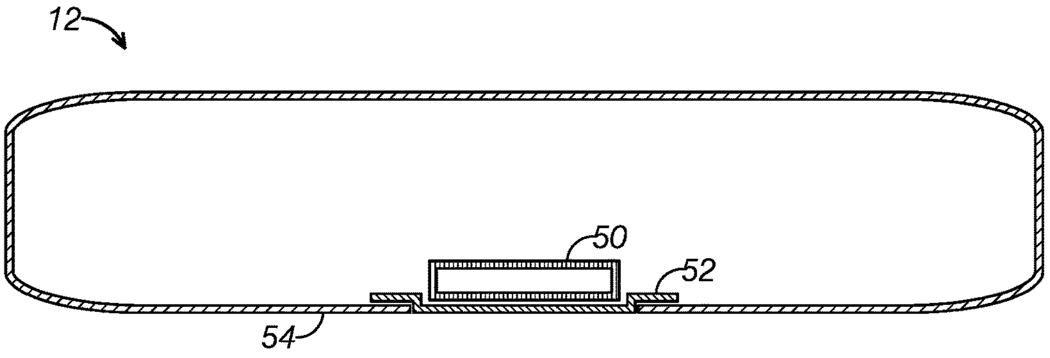
FIG. 5 illustrates a cross-sectional view of a wearable in a vicinity of an acoustic sensor, according to an exemplary embodiment of the present invention.

Referring now to FIGS. 4 and 5, the wearable 12 can include various components and/or modules. The wearable can include one or more sensors 42, typically a plurality of sensors 42 for detecting various physiological parameters of a wearer. The sensors 42 can include one or more acoustic sensors 50 which may be embedded in a protective layer 52 that facilitates sound transfer through a housing 54 of the wearable 12. The wearable 12 can further include a pre-processor 44 for sensor data, a buffer/memory 46, a main processor 48, and a main memory 58. The wearable 12 may also include an alert generation mechanism (not shown) to alert the user of a significant change in measured physiological or acoustic parameters as compared to a baseline. In some embodiments, the alert generation may be performed by an external device receiving a signal from the wearable 12. Each of these components will be discussed in greater detail below.

In some embodiments, the wearable 12 can include a data transmission module 56 for sending a signal to one or more external computing devices, such as a cloud computing device, a mobile device, a portable computer, a server, or the like, as discussed in greater detail below.

The sensors 42 in a sensor array can include one or more of the following: an accelerometer, a gyroscope, a microphone (where the microphone could be any of capacitive, piezoelectric, electro-magnetic, electret, and the like), temperature sensor (where the temperature sensor could be any of thermocouple, RTD, thermistor, infrared, and the like), vibration sensor, optical sensor (where the optical sensor can be configured for various applications) and sensors for measuring the electrical potential of the body. Some or all sensors described above can be used according to the desired accuracy and depth of information.

The array of sensors 42 capitalizes on processing by the pre-processor 44. Typically, the pre-processor 44 may be located on board the sensor 42 and/or sensor array. The extent of the pre-processing ranges from simple signal conditioning to pattern and event recognition.

Additionally, the sensor 42 and/or sensor array can include the ability to transfer data directly to memory (into the buffer/memory 46) for storage without engaging the main processor 48.

Additionally, signals from the sensors 42 may be kept separate or be combined within the sensor array to form a fusion of sensor signals.

The pre-processors 44 can be of the low power variety. While the sensors 42 may not be classified as low power, they are connected to dedicated low power pre-processors 44 for initial signal treatment.

Reduced power consumption is achieved by having the sensor data be processed at dedicated low power pre-processors 44 at first and the sensor data corresponding to events of interest are then stored directly to memory 58 and/or the buffer/memory 46. After a period of time and/or memory count, the main processor 48 can come alive to process the sensor data that has passed the basic screening of the pre-processors 44. Typically, the period of time and/or memory count is sufficient to permit the main processor 48 to be, on average, in a sleep mode for a period of time greater than then amount of time it is operating. Typically, this data is unaltered sensor data from the sensors 42, but the amount of data is reduced by the basic screening algorithm pre-processing step performed by the pre-processors 44. The reasoning is that the main processor 48 uses the most power and therefore, should run for the least amount of time possible. The main processor 48 uses the most power because it operates the main functions of the wearable 12 and the processing algorithms, for example. The pre-processor 44 on a sensor only runs a basic screening algorithm and supports memory transfer thereby qualifying it as a low power application.

The wearable 12 can transmits data via a data transmission module 56 wirelessly according to a schedule. The next major power consuming component, a radio transmitter (part of the data transmission module 56), is made into a low power component due to its very low duty cycle. While the transmitter operates to full design specifications, it does so for brief moments, resulting in reduced power consumption. By processing the signals onboard, the device derives a result and this result is simple to display, manipulate, transmit, and the like, as it is significantly less than having to output raw data streams. Hence the transmission of this brief result constitutes the extremely low duty cycle.

Figure 7:
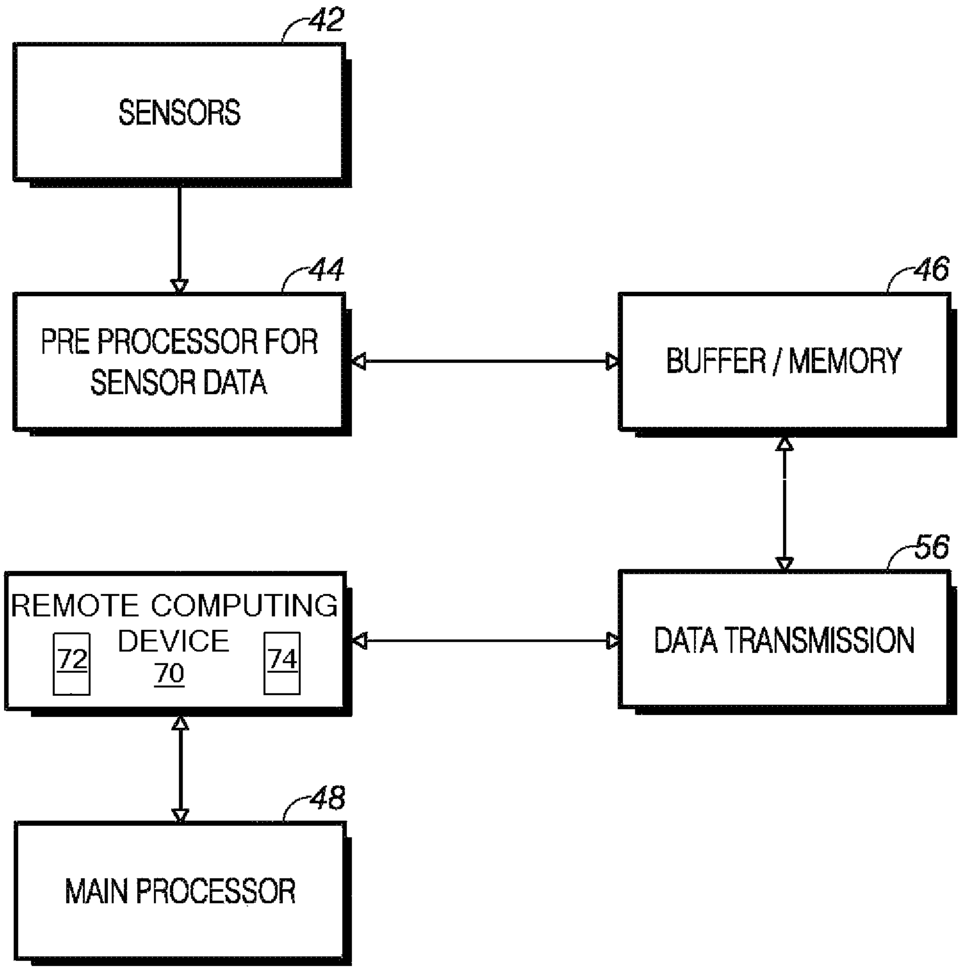
FIG. 7 illustrates exemplary processing performed by both a wearable and a remote computing device, according to an exemplary embodiment of the present invention.

In some embodiments, as shown in FIG. 7, the wearable 12 can transmit pre-processed data periodically, such as after a period of time and/or a predetermined memory count, via the data transmission module 56 to a remote computing device 70, such as a cloud computing environment 72, a mobile device 74, or the like. The function of the main processor 48, described above, may be performed by the remote computing device, thus not requiring the wearable 12 to perform the more power consumptive main processing algorithms. In some embodiments, should any of the processed data result in the need to alert the user, the remote computing device can send a signal to the wearable 12 to alert the user.

In some embodiments, the wearable 12 can continuously, in real-time, transmit pre-processed data to the remote computing device. While this mode may be more power consumptive, the power saved by not requiring use of the main processor 48 may offset the power needed for continuous use of the wireless radio.

The data transmission module 56 can transmit data in various methods, including Wi-Fi®, Bluetooth®, 4G, 5G, or the like. The wearable 12 may further include a port (not shown) to provide for wired communication to the remote computing device 70.

In some embodiments, the wearable 12 may provide, on-board, both the functions of the pre-processor and the main processor, as discussed above, where the wearable 12 can send the data from the main processor (which is typically the original data stream from the sensors, with data removed via both the pre-processing and the main processing algorithms) to the remote computing device for additional post-processing, where the remote computing device may use an even more robust algorithm for identifying or classifying the event of interest.

As used herein, the event of interest may be cough, a heart rhythm (or disarrythmia), wheezing, rales, or any other detectable cardio pulmonary event. The algorithm may be built into the wearable 12, where the wearable 12 is designed for detecting one or more particular events of interest. In other embodiments, the wearable 12 may be user-loaded with an algorithm, where the wearable 12 can be configured for the detection of a user-selected event of interest, depending on the particular algorithm(s) selected by the user from one or more of a plurality of user selected algorithms. These algorithms include both the basic screening algorithm (for use by the pre-processor), and the main algorithm, for use by the main processor, when present on the device, as discussed above. The user selected algorithms may be provided, for example, from a store or database of algorithms from which the user can select.

Additionally, the power management algorithm is able to shed functions as battery power runs low, thereby achieving a longer runtime on the remaining power.

The methodology applied here to reduce power consumption extends beyond simply using low power components but rather governs the processes and architecture of the wearable 12.

Communication with external devices and environment for setup, information relaying, upgrades, and the like, is done via a physical port (not shown, but may be, for example a micro and/or mini USB port), wirelessly via Bluetooth Low Energy, Bluetooth regular, Machine-to-machine (cellular based), Body Area Networks, ZigBee, and the like, and the method is determined by the application. Wireless communications may be direct to an end point or a relay unit and, as such, would incorporate the requisite antenna. One or more communication methods may be built-in to the wearable 12.

While the wearable 12 is intended to be worn against the body and while there is no substantial evidence to show that the above radio communication causes bodily harm, the wearable 12 may incorporate an added step to reduce exposure. Wireless infrastructure comes alive on a schedule that is user settable but ranging from once every fifteen minutes to once every two hours, for example. By having such a procedure, the body is exposed to radio signals emanating from the device only at those times. Further still, the length of the transmission during these times are estimated at no more than ninety seconds, for example, at design power.

The communication range of the wearable 12 depends on its operation. For setup and visualization of the output data, the wearable 12 can be connected to a smartphone or smart device via Bluetooth and or Bluetooth Low Energy architecture, for example. For setup and visualization of output data when a smartphone or smart device is not available or out of range, the device can connect via a cellular service to an end point, relay unit or data service. In this instance, the data is re-routed to a smartphone or smart device and is also available via a web portal.

Regardless of mode, the device sends alerts via all communication modes thereby increasing the range beyond Body Area Networks, Bluetooth and BTLE, node to node Wi-Fi, or the like.

The wearable is fully autonomous when compared with current devices in the market. The current thought is that processing is power hungry and so sensor data is transmitted in real time to another device for processing or uploaded periodically for processing. The wearable is then essentially tethered to another device to complete the analysis of the sensor data, rendering it simply as a data acquisition device. In this embodiment, the wearable 12 of the present invention is able to process the sensor data according to stored algorithms to arrive at a result and further still, investigate this result whether as an instance or with a set of prior results to render a decision inclusive of generating alerts.

This process works by having the having the sensor outputs coupled to fast low power processors, such as pre-processors 44, running qualification or filtering algorithms the eliminate sensor information that has less than 50% to 80% resemblance to sensor data that is of use. An algorithm capable qualifying the sensor data in this manner generally requires significantly less power to run as compared to an algorithm providing a response with less than 2% error. The selected data is stored immediately in equally fast memory, such as buffer/memory 46, where it is kept until the memory is full or a specified time has lapsed, whichever occurs first. At this moment, the main processor 48, running a very accurate algorithm, is called into operation to process the stored sensor data. Where information of interest occurs intermittently, this can result in only 10% to 30% of a period of time containing such information. Therefore, the main processor 48 operates less, saving power significantly. This forms the basis for an autonomous wearable operating for comparable times as those that are not but requires real time data transfer to another device.

Autonomy as implemented above is unique and positions the wearable 12 for use in many applications where audio events, motion events or combination audio and motion events are being monitored in real time. Interestingly, the very reason current real time monitoring products are tethered to another device, i.e., to save on power consumption, is the reason that full onboard processing is implemented resulting in autonomy, i.e., to save on power consumption.

The low power consumption results in the possibility to use smaller batteries; the distributed processing resulting in the need for less powerful processors; the use of new sensors in miniature packaging, recent advances in miniaturization, and the like, all play a role in the resultant physical properties of the wearable 12. The device is comparable in size and weight to other wearables in the market while these wearables are really just remote sensors, as explained above.

Figure 6:
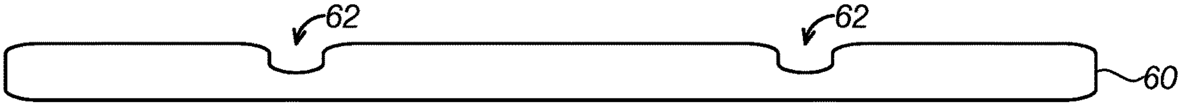
FIG. 6 illustrates a side view of a wearable housing, showing reduced thickness areas to help facilitate flexing with body movements, according to an exemplary embodiment of the present invention.

The small form factor plays a significant role in wearability as well as innovative approaches to manufacturing. The wearable 12 can utilize recent advancements in flexible circuit boards and flexible batteries. All three coupled together results in a wearable that could conform to the body's contours as it is in motion, resulting in less awareness of the wearable's presence. While current manufacturers are continuing development in hard housings, the wearable 12, according to embodiments of the present invention, is encapsulated in robust yet soft materials reducing the sensation of it against the skin. As shown in FIG. 6, the housing material 60 of the wearable 12 can include reduced thickness areas 62 to facilitate flexing with body movement.

Additionally, the wearable 12 is designed to accommodate various adhesives being stuck to it for subsequent adhesion to the skin. The lightweight characteristics of the wearable 12 means that adhesives, such as adhesives 14, 18 of FIG. 3, can be of the easy to peel variety unlike adhesives of many current wearables.

As discussed above, the wearable 12 has a main processor 48 or processors to control the operation thereof, execute the processing of signals, execute algorithms utilizing signal data and or stored data, execute power management, memory management, user interactions, wireless communications and any other processes and or functionality.

The processor 48 may be of the low power consumption variety and when it is such, the device has longer runtimes. Additionally, the processor 48 can be set to execute programs or applications on demand rather than having to execute an instruction set comprising most or all of the functionality.

Additionally, the programs or applications as well as the processor's operating system may be modified, changed or updated even after being set into operation. Such an approach allows for the device to be adopted for many uses as well as capitalize from automatic remote bug fixes and or functionality enhancement.

By processing the signals onboard, the wearable 12 derives a result and this result is simple to display, manipulate, transmit, and the like, as it is significantly less than having to output raw data streams.

In other words, the main processor 48 and the communication module 56 may operate periodically. As used herein, a periodic operation of a component of the wearable 12 means that the component operates less than 50 percent of the time of use thereof, typically less than 25 percent of the time of use thereof, and usually less than 10 percent of the time of use thereof. For example, as discussed above, the wireless infrastructure can come alive on a schedule that is user settable but ranging from once every fifteen minutes to once every two hours, for example. Further still, the length of the transmission during these times are estimated at no more than ninety seconds, for example, at design power. This results in, for example, ninety seconds of data communication within a period of 15 minutes (where periodically here means 10 percent of the time) to 2 hours (where periodically here means 1.25% of the time).

Cough is an audible symptom and most manufacturers have adopted strictly audio based methods to identifying it. In the wearable 12 of the present invention, audio based cough recognition algorithms are utilized alongside motion associated with coughs. By combining the two, ambient coughs, i.e., coughs not originating from the user, are rejected as corresponding cough motions are not detected. While this seems logical, previous attempts at this were not fruitful as the wearable then required specific alignment for operation. With the wearable 12 of the present invention, sensor orientation is corrected for by other sensors like gyroscopes. Additionally, recent development into nine-degrees of freedom sensors now make is possible to accurately capture useful motion data which the wearable 12 can utilize.

The current cough devices are prone to false positives, require bulky computers for processing and some even require a human element to double check. The wearable 12 capitalizes on learning iterations that are a standard feature of audio event recognition algorithms to hone its skills in cough recognition.

When the wearable 12 is being worn, it doubles over as an electronic stethoscope but more importantly, picks up sounds outside of human hearing which is important for recognizing patterns. The versatility of the algorithms means that the wearable could be programmed to detect and record almost any acoustic physiological symptom or event that could be collected from the region of the upper torso.

Currently, there are no multi sensor wearables in the market that also incorporates real time detection and monitoring of audio based signals from the upper torso regions. This holds for fully autonomous wearables as well.

The wearable 12 can be further equipped for detecting and recording heartbeat rate via audio and vibration methods.

The wearable 12 can be further equipped for detecting and recording body skin temperature via any of thermocouples, thermistors, infrared, and the like.

EXAMPLE

Asthma Application

The wearable 12 can be used in various applications. One such application is the detection of an asthmatic attack prior to its occurrence. Conventionally, asthma monitoring was focused on symptoms evident during an attack and not prior to it; acoustic monitoring for health solutions are focused on replicating the performance of a stethoscope; detached sensors are prone to picking up ambient noises to the extent that target signals are obscured; some physiological symptoms require multiple sensor types to simultaneously record various components of the symptoms to confirm the symptom. The wearable 12 addresses these pitfalls of conventional devices.

Traditionally, the symptoms monitored to indicate an asthmatic attack, whether self-monitoring or with the aid of a device, have always been those associated with an ongoing attack. The primary reason being that they were the easiest to spot and they required the simplest technology when needed. For example, an attack is determined by a self-monitoring method of identifying wheezing or determined by a device monitoring method of identifying lung function changes via a spirometer. These classic symptoms were chosen to match the availability of technology or ease to understand, but they are all symptoms of an ongoing attack which is more of a reactive approach.

Embodiments of the present invention focus on symptoms that manifest at the onset of an attack which is typically well before the traditional symptoms found during the attack—an asthmatic attack builds up over time. The approach is proactive as compared to the traditional reactive methods. Knowing the indicators earlier enables remedial action before the situation is exacerbated. These symptoms, while well known, were difficult to identify and monitor without the use an extensive array of equipment in constant attendance. The wearable 12 of the present invention has miniaturized the equipment set facilitating constant use in a non-invasive manner.

The stethoscope is unsurpassed when it comes to listening to the human body because it is in direct contact with the body and the sounds are amplified and transmitted directly to the listener. In essence, the listener hears practically the entire audible spectrum without any significant loss. The stethoscope is key for a physician to pick up and determine the severity of Asthma related symptoms. The problem with us utilizing an existing digital stethoscope is that we would require sophisticated pick up microphones, full spectrum amplifiers and digital signal processing capability for high quality signals—these features are required to emulate a simple stethoscope. For Asthma symptom monitoring, one does not need full spectrum microphones and signal processing—just for the frequency range that is required. Embodiments of the present invention remove excess capability that results in reduction in size, process requirements, power consumption—in essence, it results in an ultra-portable stethoscope optimized for audible Asthma symptoms. Without this, the wearable 12 may have problems with size, power consumption, relevance, cost, and the like.

Current methods in the market to sense and measure the symptoms associated with asthma are prone to picking up and measuring excessive and false data. For example, built-in microphones from smart phones or other devices pick up ambient noises even if they are worn in clothing pockets or secured with bands. Likewise, microphones in earpieces also do the same. Accelerometers from the smart devices worn in pockets, strapped on with bands, or the like, all pickup additional motion, introducing errors. Accelerometers in devices secured to the hand pick up even more extraneous data. Non-contact sensors reduce the ability for complete mobility unless the non-contact sensor unit accompanies the user, which is impractical.

The wearable 12 of the present invention can position the sensors and secure them in the optimum positions so that extraneous, ambient and false readings are reduced significantly. Further still, by being firmly attached to the user, the range of signals are limited to those possible from the human body, for the most part. The wearable therefore solves the problem of having false and nuisance signals as well as facilitates the pick-up of symptoms where a physician will look for them.

The available devices on the market that could have been used with some modifications, i.e., the addition of missing sensors, are limited in their architecture when it comes to picking up human body symptoms. Most symptoms are composed of multiple parameters, e.g., breathing involves motion, sound and vibration, or say coughing which involves sound, motion and vibration. To pick these symptoms up, the use of signals from more than one type of sensors is required and these signals must be in time with each other. Similarly, the processing to identify the symptom must be done on each signal and the processing is generally different for each signal. Available devices are unable to achieve this in an efficient manner that supports implementation as a wearable.

The wearable 12 of the present invention can include various sensors built-in in the first instance and they are all picked up, sampled, measured, stored and processed so that the integrity of them are preserved to arrive at the conclusion that the symptom is picked up and identified.

While the above description of the wearable 12 targets respiratory diseases, the wearable 12 of the present invention can be used for cardiology, fitness, and other health/biometric requirement for humans, livestock and other animals. Additionally, the device could be used for any application that recognizes a particular sound, e.g., gunshot monitoring in cities, chain saws in forests, mining activities, gunshot monitoring in reserves and parks, monitoring arrival of migratory animals, SIDS research, and the like.

While the intended application is a wearable, from the above, it could be packaged for outdoor mounting in all weather conditions as well as for indoor mounting.

While the above description describes cough as an event of interest related to respiratory diseases, the event of interest for the device to detect can include other heart or lung sounds, such as wheezing, rales, or the like.

While the above description describes an on-body monitoring device that can make continuous measurements for a plurality of days, in some embodiments, the device may be used both for on-body monitoring and instance monitoring. In this embodiment, lung sounds may be captured by the on-body functioning of the device, as discussed above. However, when the user does not want to or cannot wear the device on-body on a given day, the user can perform one or more spot readings. Such spot readings may be obtained, for example, by the user breathing onto the device so it can capture spot info. During these days, one or more spot readings would provide at least some data, an improvement on getting no readings over a particular time period. The wearable could pick up the data if the user blows or breathes on it or adjacent to it, for example.

Figure 8:
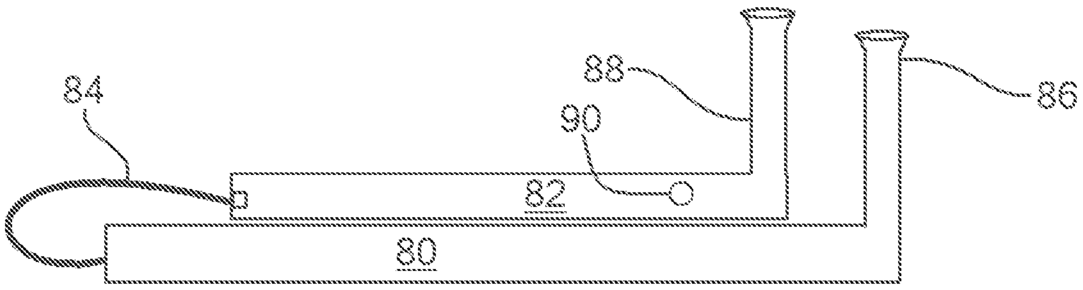
FIG. 8 illustrates a schematic representation of a wearable device in a charging base with various spot measurement applications shown.

Referring to FIG. 8, in another embodiment, a wearable 82, similar to the wearables discussed above, could be in a charging cradle 80, which may connect to the wearable 82 via a charge cable 84, or may provide wireless charging, for example. The charging cradle 80 could include a mouthpiece 86 to channel a user's breathing in order to be detected by the connected wearable 82. In another embodiment, a mouthpiece unit 88 could made to removably attach to the wearable 82. In yet another embodiment, the wearable could have a thru hole aperture 90 to allow breathing there through. While FIG. 8 shows mouthpiece 86, mouthpiece unit 88 and aperture 90, it should be understood that one or more of these features can be incorporated into various aspects of the present invention.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A physiological monitoring system comprising:

a wearable comprising:

at least one sensor for measuring a physiological parameter of a user;

an acoustic sensor for receiving an acoustic signal;

a pre-processor operable to receive data from the at least one sensor and the acoustic sensor, the pre-processor performing a basic screening algorithm on original signals from the at least one sensor and the acoustic sensor to detect an event of interest as a screened signal, the basic screening algorithm eliminating a portion of the original signals from the at least one sensor and the acoustic sensor that fail to meet predetermined criteria for detecting the event of interest, the screened signal being the original signals with the portion removed therefrom;

a buffer/memory for storing the screened signal after being processed by the pre-processor; and a main processor having a main processor algorithm operable to periodically process, based on a memory count or a period of time, the screened signals to verify that the screened signals include the event of interest, the main processor algorithm operating at greater accuracy for detecting the event of interest than the basic screening algorithm, wherein the wearable performs continuous monitoring for the event of interest measured in whole days.

2. The system of claim 1, wherein the pre-processor operates at a first power consumption level and the main processor operates at a second power consumption level, greater than the first power consumption level.

3. The system of claim 2, wherein the at least one sensor comprises a motion sensor.

4. The system of claim 1, wherein the at least one sensor, the acoustic sensor, the buffer/memory and the pre-processor are integrated into a single wearable device.

5. The system of claim 4, wherein the acoustic sensor is embedded in a protective layer that facilitates sound transfer through a housing of the wearable device.

6. The system of claim 5, wherein the housing includes one or more regions having a reduced thickness as compared to the remainder of the housing to permit flexing thereof when attached to the user.

7. The system of claim 1, further comprising a main memory for storing a processed signal after being processed by the main processor.

8. The system of claim 1, wherein the acoustic signals are detected and recorded directly from a surface of the user between a waist and a base of a neck of the user.

9. The system of claim 1, wherein the signals from the at least one sensor and the acoustic sensor that fail to meet predetermined criteria for detecting the event of interest are those that have less than 50% to 80% resemblance to sensor data that is relevant for detecting the event of interest.

10. The system of claim 1, wherein the basic screening algorithm of the pre-processor and the main processor algorithm are provided by one of a plurality of user selected algorithms, the one of the plurality of user selected algorithms detecting a user-selected event of interest, depending on a selected one of the plurality of selected algorithms.

* * * * *